United States Patent [19]

Randklev

[11] Patent Number: 4,503,169
[45] Date of Patent: Mar. 5, 1985

[54] RADIOPAQUE, LOW VISUAL OPACITY DENTAL COMPOSITES CONTAINING NON-VITREOUS MICROPARTICLES

[75] Inventor: Ronald M. Randklev, White Bear Lake, Minn.

[73] Assignee: Minnesota Mining and Manufacturing Company, St. Paul, Minn.

[21] Appl. No.: 602,114

[22] Filed: Apr. 19, 1984

[51] Int. Cl.³ .......................... A61K 6/08; C08K 3/36; C08L 35/02
[52] U.S. Cl. ...................... 523/117; 106/35; 260/998.11; 433/228; 501/103; 501/133; 523/115
[58] Field of Search ............... 433/228; 260/998.11; 106/35; 523/115, 117; 501/103, 133

[56] References Cited

U.S. PATENT DOCUMENTS

| | | | |
|---|---|---|---|
| 3,066,112 | 11/1962 | Bowen | 523/116 |
| 3,539,533 | 11/1970 | Lee et al. | 524/560 |
| 3,629,187 | 12/1971 | Waller | 523/115 |
| 3,709,706 | 1/1973 | Sowman | 501/103 |
| 3,709,866 | 1/1973 | Waller | 523/115 |
| 3,751,399 | 8/1973 | Lee et al. | 526/232 |
| 3,766,132 | 10/1973 | Lee et al. | 523/116 |
| 3,793,041 | 2/1974 | Sowman | 501/103 |
| 3,795,524 | 3/1974 | Sowman | 501/95 |
| 3,860,529 | 1/1975 | Hamling | 501/103 |
| 3,860,556 | 1/1975 | Taylor | 523/116 |
| 3,911,581 | 10/1975 | Dietz | 523/117 |
| 4,002,669 | 1/1977 | Gross | 560/126 |
| 4,115,346 | 9/1978 | Gross | 523/116 |
| 4,150,012 | 4/1979 | Joos | 260/998.11 |
| 4,166,147 | 8/1979 | Lange | 428/328 |
| 4,217,264 | 8/1980 | Mabie et al. | 501/94 |
| 4,220,582 | 9/1980 | Orlowski et al. | 433/228 |
| 4,259,117 | 3/1981 | Yamauchi et al. | 106/35 |
| 4,292,029 | 9/1981 | Craig | 433/228 |
| 4,297,266 | 10/1981 | Ibsen et al. | 260/998.11 |
| 4,302,376 | 11/1981 | Walkowiak et al. | 106/35 |
| 4,306,913 | 12/1981 | Mabie et al. | 106/288 B |
| 4,327,014 | 4/1982 | Kawahara et al. | 523/116 |
| 4,379,695 | 4/1983 | Orlowski et al. | 433/217 |
| 4,387,240 | 6/1983 | Berg | 556/440 |
| 4,404,150 | 9/1983 | Tsunekawa et al. | 433/226 |
| 4,407,984 | 10/1983 | Ratcliffe et al. | 433/228 |

FOREIGN PATENT DOCUMENTS 2115799 9/1983 United Kingdom .

OTHER PUBLICATIONS

Mabie and Menis, J. Biomed Mats. Res., 12, 435–72, (1978).

Primary Examiner—Ronald W. Griffin
Attorney, Agent, or Firm—Donald M. Sell; James A. Smith; David R. Cleveland

[57] ABSTRACT

Radiopaque, low visual opacity dental composites and non-vitreous microparticles for use therein, the microparticles individually containing amorphous silica microregions interspersed with radiopacifying polycrystalline ceramic metal oxide microregions, the microparticles being substantially free of visually opacifying inclusions such as crystalline microregions having diameters greater than about 0.4 micrometers.

20 Claims, 1 Drawing Figure

RADIOPAQUE, LOW VISUAL OPACITY DENTAL COMPOSITES CONTAINING NON-VITREOUS MICROPARTICLES

TECHNICAL FIELD

This invention relates to composites containing non-vitreous microparticles. In another aspect, it relates to novel non-vitreous microparticles for use in such composites, and to a process for making such composites.

BACKGROUND ART

A variety of references have described non-vitreous small particles, e.g., U.S. Pat. Nos. 3,709,706, 3,793,041, 3,795,524, 4,166,147, 4,217,264, and 4,306,913 and U.K. published patent application no. 2,115,799. Some of the small particles described in such references are combined with binders (e.g., polymerizable resins) to form composites, and a few of such small particles may contain sufficient amounts of a suitable ceramic metal oxide to render composites which might be made with such particles opaque to X-ray radiation (i.e., radiopaque).

Radiopacity is a very desirable property for dental composites. Radiopaque composites can be examined using standard dental X-ray equipment, thereby facilitating long term detection of marginal leakage or caries in tooth tissue adjacent to the cured composite. However, a dental composite should also have low visual opacity, that is, it should be substantially transparent or translucent to visible light. Low visual opacity is desired so that the cured dental composite will have a lifelike lustre. If such a dental composite is intended to be cured or polymerized using visible light-induced photoinitiation, then the depth of cure required (sometimes as much as two millimeters or more), the desire for uniform hardness in the cured composite, and the physical limitations imposed by carrying out the curing reaction within the mouth (which require, among other things, that the uncured composite usually be exposed to light from only one angle, and that the curing radiation be provided by a portable instrument) all mandate that the composite have low visual opacity to enable deep, thorough cure.

An additional desirable property for dental composites is durability. Durability sometimes can be improved by increasing the percentage of filler particles in the composite. However, increased filler levels typically lead to increased visual opacity, thus reducing translucency and limiting visible-light cure depth and cure uniformity.

A further desirable property for dental composites is cure stability. For a two-part non-light cure dental composite (i.e., a so-called "chemical cure" composite), cure stability is evaluated by comparing polymerization set times for aged and unaged composite samples when the two parts of the composite are mixed together. For a one-part light-cure dental composite, cure stability is evaluated by comparing top and bottom hardnesses of composite samples that have been aged or are unaged and are cured to a standard depth. Poor cure stability is manifested by a change in polymerization set time or a difference in top and bottom cure hardness between aged and unaged composite samples. The filler particles in a dental composite sometimes interact with the other ingredients of the composite (e.g., with the polymerizable resin or the polymerization initiators) and adversely affect cure stability. These interactions can be unpredictable and are sometimes poorly understood.

In practice, it has proven very difficult to formulate dental composites having a commercially useful combination of high radiopacity, low visual opacity, high filler loading, and cure stability.

SUMMARY OF THE INVENTION

The present invention provides, in one aspect, a radiopaque dental composite, comprising a mixture of (a) polymerizable resin suitable for use in the oral environment, and (b) non-vitreous microparticles, said microparticles individually comprising:

(i) a plurality of amorphous microregions comprising oxide of silicon, substantially uniformly interspersed with (ii) a plurality of crystalline microregions comprising radiopacifying polycrystalline ceramic metal oxide, said microparticles being substantially free of visually opacifying inclusions.

In addition, the present invention provides novel microparticles useful in such composites, and a process for making such composites.

Other workers interested in making small particles for use in dental composites, e.g., those described in said U.S. Pat. Nos. 4,217,264 and 4,306,913, and said U.K. published patent application no. 2115799 have apparently sought to make such particles entirely amorphous in order to provide a good refractive index match between the small particle and the resin. The metal oxide used in such small particles typically have refractive indices greater than two, a value which greatly exceeds the refractive indices of conventional resins. In contrast to the approach of such other workers, the present invention provides microparticles which deliberately contain both amorphous and crystalline microregions. Dental composites having low visual opacity are obtained by ensuring that the microparticles are substantially free of visually opacifying inclusions. In a preferred embodiment, substantially all of the crystalline microregions of such microparticles have diameters less than about 0.4 micrometers.

BRIEF DESCRIPTION OF THE DRAWING

The accompanying drawing is a transmission electron micrograph of an $SiO_2:ZrO_2$ microparticle (prepared in Example 1) at a magnification of 300,000×.

DETAILED DESCRIPTION OF THE INVENTION

The term "radiopaque", when used to describe the dental composites of the present invention, refers to a cured composite exhibiting sufficient opacity to X-radiation to enable the composite to be distinguished from tooth structure using standard dental X-ray equipment. The desired degree of radiopacity will vary depending upon the particular application and the expectations of the practitioner evaluating the X-ray film. A preferred degree of radiopacity can be measured using the following test. A conventional dental X-ray film is exposed through a one mm thick cured layer of composite using a conventional radiation time and intensity. The X-ray negative is developed and its density evaluated using a Macbeth Transmission Densitometer, Model TD 504, equipped with a visible light filter. Preferably, the indicated densitometer reading will be about 1.4 or less, more preferably 0.8 or less.

A "dental composite", as used herein, refers to a hardenable (or hardened) composition containing polymerizable (or polymerized) resin(s), filler particles of one or more types, and any desired adjuvants, the resulting composite being suitable for use in the mouth. Dental composites of the present invention can be multiple part chemical cure or one part UV- or visible-light cure compositions. The dental composites of the present invention find particular use as anterior or posterior restoratives, cavity liners, orthodontic bracket adhesives, crown and bridge cements, artificial crowns and casting resins.

Polymerizable resins suitable for use in the dental composites of the present invention are hardenable organic resins having sufficient strength, hydrolytic stability, and non-toxicity to render them suitable for use in the oral environment. Examples of such resins include acrylate, methacrylate, urethane, and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof. A preferred polymerizable resin for use in the present invention is a mixture of diglycidylmethacrylate of Bisphenol A (frequently referred to as "BIS-GMA") and triethyleneglycol dimethacrylate (frequently referred to as "TEGDMA").

A "non-vitreous" microparticle, as used herein, is a small diameter particle (preferably having a diameter less than about 50 micrometers) which has not been derived from a melt. A "microregion" is a portion of the microparticle which when observed using transmission electron microscopy at a magnification of about 100,000 to 1,000,000 appears uniformly shaded (or generally uniformly shaded) and appears to contain a single crystalline or amorphous inorganic species. The microparticles of the invention can be characterized by the presence of a plurality (i.e., two or more) of at least two distinctly different types of microregions within individual microparticles when so observed. The two types of microregions are referred to herein as "amorphous microregions" and "crystalline microregions". The amorphous microregions are substantially uniformly interdispersed with the crystalline microregions; that is, the amorphous and crystalline microregions are substantially randomly arrayed throughout individual microparticles. In order to examine individual microparticles, a representative sample (e.g., 10–100) of the microparticles should be studied, and sintering bonds which may agglomerate individual microparticles together should be fractured, e.g., by mild pulverization.

The presence of amorphous and crystalline microregions in the microparticles can be further determined using X-ray or electron diffraction or other techniques suitable for examination of small amorphous or crystalline species. Crystalline microregions are those which, when examined using X-ray or electron diffraction analysis, exhibit a characteristic distinguishing pattern of diffraction lines. Amorphous microregions are those which, even when present in an array of such microregions and observed using X-ray or electron diffraction analysis, do not exhibit distinguishable lines. Because the microparticles of this invention contain both amorphous and crystalline microregions, the microparticles as a whole will exhibit a diffraction pattern. The presence of amorphous microregions in the microparticles is ascertained by the absence of the characteristic diffraction pattern for the chemical species making up the amorphous microregion. Preferably, the amorphous microregions have diameters less than about 0.1 micrometers, and more preferably have diameters of about 0.002 to 0.05 micrometers.

A "radiopacifying" metal oxide is an inorganic oxide which, when present in the microparticles of this invention, inhibits the transmission of X-ray radiation through the microparticles to a degree sufficient to render usefully radiopaque a dental composite made therewith. A "polycrystalline" metal oxide has a sufficient number of like crystalline microregions such that the unit cell structures thereof can be discerned or identified by examining the microparticles using X-ray or electron diffraction analysis. Typically, the crystalline microregions will represent about one-half volume percent or more (preferably five volume percent or more) of the total volume of the microparticle. The actual volume percent will depend upon the type and amount of metal oxide employed. Preferably, the crystalline microregions have diameters less than about 0.05 micrometers, and more preferably have diameters of about 0.001 to 0.01 micrometers, as determined using X-ray or electron diffraction analysis.

A "ceramic" metal oxide is an organic oxide which, when in its pure form, can be fired or sintered into a rigid or self-supporting polycrystalline form that is stable in a normal air environment, e.g., 23° C. and 50 percent relative humidity. Suitable ceramic metal oxides are non-toxic when incorporated into the microparticle and are colorless or only weakly colored, e.g., $BaO$, $Bi_2O_3$, $CaO$, $Nb_2O_5$, $Sb_2O_5$, $SnO_2$, $Ta_2O_5$, $TiO_2$, $Y_2O_3$, $ZnO$, $ZrO_2$, and oxides of the lanthanide series (e.g., $CeO_2$, $Ce_2O_3$ and $La_2O_3$), as well as mixtures and mixed oxides thereof. Preferred ceramic metal oxides include $HfO_2$, $La_2O_3$, $SrO$, $ZrO_2$, and mixtures thereof, with $ZrO_2$ being most preferred. Characteristically, substantially all (e.g., 90 weight percent or more) of the radiopacifying ceramic metal oxide in the microparticle is present in its polycrystalline form, and substantially none (e.g., 10 weight percent or less) is present in an amorphous form.

A preferred method for preparing the microparticles of the present invention, referred to herein as a "sol-gel" method, involves the combining of (1) an aqueous or organic dispersion or sol of amorphous silica with (2) an aqueous or organic dispersion, sol, or solution of the desired radiopacifying ceramic metal oxide or a precursor organic or inorganic compound which is calcinable to the desired radiopacifying ceramic metal oxide. For brevity, the aforementioned dispersion or sol of silica will be sometimes referred to hereafter as the "silica starting material", and the aforementioned dispersion, sol, or solution of the radiopacifying ceramic metal oxide or precursor compound will sometimes be referred to hereafter as the "ceramic metal oxide starting material". The mixture of silica starting material and ceramic metal oxide starting material is dried to a solid, ground, fired, and reground to form microparticles of the invention. The microparticles can then be combined with an appropriate resin to form a composite of the invention.

Although either aqueous or organic silica starting materials can be employed in the sol-gel method, aqueous silica starting materials are preferred for reasons of economy. Suitable aqueous silica starting materials preferably contain colloidal silica at concentrations of about 1 to 50 weight percent, more preferably 15 to 35 weight percent. Suitable organic silica starting materials include organosols containing colloidal dispersions of silica in organic solvents (preferably water-miscible polar organic solvents) such as ethanol, normal or isopropyl alcohol, ethylene glycol, dimethylformamide and the various "Cellosolve" glycol ethers. The size of the colloidal silica particles in the silica starting material can vary, e.g., from 0.001 to 0.1 micrometers, preferably about 0.002 to 0.05 micrometers.

Preferred silica starting materials which can be used in this invention include aquasols sold under the trademark "Ludox" from E. I. DuPont de Nemours and Co. Other useful silica starting materials include dispersions or aquasols sold under the trademarks "Nalco", "Syton" and "Nyacol". Additional suitable commercially available silica starting materials are listed in said U.S. Pat. Nos. 3,709,706 and 3,793,041.

Preferably, the silica starting material is filtered to remove extraneous solids, bacterial growth and other impurities. More preferably, the silica starting material is filtered through a microfine filter, as described in more detail below. If described, the silica can be modified by addition of other inorganic compounds, for example, those compounds (e.g., $B_2O_3$) which can form amorphous microregions under the conditions used to prepare the microparticles of the present invention. It should be borne in mind that the addition of such inorganic compounds may alter the refractive index of the final microparticles, and may effect the visual opacity of a dental composite prepared therewith.

Although either aqueous or organic ceramic metal oxide starting materials can be employed in the sol-gel method, aquasols are preferred for reasons of economy. Suitable commercially available ceramic metal oxide aquasols include $CeO_2$, $Sb_2O_5$, $SnO_2$, and $ZrO_2$ aquasols. Commercial $ZrO_2$ aquasols typically contain a small amount (e.g., 1 to 3 weight percent) of $HfO_2$ as a contaminant. Suitable calcinable precursor compounds preferably are carboxylates (e.g., acetates, formates, oxalates, lactates, propylates, citrates, or acetylacetonates) or salts of mineral acids (e.g., nitrates), selection of particular precursor compounds being dictated by availability and ease of handling. Use of precursor compounds which might form precipitates or undesired crystalline microregions prior to gelation, or form water- or acid-soluble compounds or colored impurities in the microparticles, preferably should be avoided. Representative precursor compounds useful in the present invention include barium acetate, lanthanum nitrate, strontium nitrate, tantalum nitrate, and zirconium acetate.

Other metal oxides which may not themselves provide sufficient radiopacity can, if desired, be included in the microparticles of the present invention. Such other metal oxides can be useful, for example, to adjust various physical properties of the microparticles (e.g., refractive index, hardness, density or porosity) or physical properties of dental composites prepared therewith (e.g., viscosity before cure, or compressive strength, tensile strength, or visual opacity after cure). Such other metal oxides include $Al_2O_3$ and CaO. When the above-described sol-gel method of preparation is employed, such other metal oxides can be introduced into the final microparticles by combining a dispersion or sol containing the desired other metal oxide (or a suitable dispersion or sol containing a precursor compound calcinable thereto) with the silica starting material and ceramic metal oxide starting material. If desired, such other metal oxides can be introduced by using a silica sol containing silica particles coated with such other metal oxide (e.g., "Nalco" 612 or 613 alumina-coated silica aquasols).

In a most preferred embodiment, the sol-gel method is carried out as follows. First, an aquasol containing colloidal silica is mixed with a rapidly stirred sol or solution containing the desired radiopacifying ceramic metal oxide (e.g., $ZrO_2$) or calcinable precursor compound (e.g., zirconium acetate). For some starting materials, reverse order of addition can lead to non-uniform interspersal of the amorphous and crystalline microregions in the final microparticle. The mixture preferably should be sufficiently acidic to prevent non-uniform gelation from occurring. For example, the pH preferably is below about 4.5 for a silica:zirconium acetate mixture. The mixture is then gelled, e.g. by raising the pH, by dehydration (using, for example, a "Rotovap" apparatus), or by heating the mixture at a temperature below its boiling point. For example, dehydration by heating below about 75° C. can be used for a silica:zirconium acetate mixture.

The gel may contain a significant portion of the water or other solvents present in the starting materials. The gel is heated at a temperature and pressure sufficient to remove the water or solvents without causing boiling of the gel, e.g., for 20-24 hours at 75° C. and ambient pressure, thereby yielding a dried or substantially dried solid. Drying preferably is carried out in shallow pans. The dried solid breaks up into small granules. The small granules preferably are pulverized or comminuted to facilitate removal of organic compounds. The granules are then heated at a temperature and pressure sufficient to remove substantially all such organic compounds, e.g., in air at atmospheric pressure for 2-4 hours at 200°-600° C., preferably 300°-600° C. Differential thermal analysis or gravimetric analysis can be used to determine the extent of organic compound removal. The resulting powder is very friable and can be further pulverized.

The powder is next fired at a temperature and for a time sufficient to convert the ceramic metal oxide or precursor to polycrystalline ceramic metal oxide. The firing time and temperature should not be excessive, as it is desirable to retain oxide of silicon in its amorphous state, prevent the growth or formation of crystalline microregions having diameters greater than about 0.4 micrometers, and densify the microparticles to reduce the incidence of voids. During the firing cycle, the microparticles will undergo significant changes in density, surface area, pore volume and pore size. Density tends to increase during firing, while surface area and pore volume tend to decrease. For example, in 5.5:1 mole ratio $SiO_2:ZrO_2$ microparticles, density reaches about 2.50 gm/cc after firing to about 1000° C. Surface area reaches a maximum after firing to 400° C. (at a value of about 175-200 $m^2/g$ as measured by the BET method), declines after firing to 950° C. (to a value of about 50-75 $m^2/g$), then declines further after firing to 1000° C. (to a value of about 4-6 $m^2/g$). Average pore volume reaches about 40% of the microparticles (as determined using the BET method) after firing at 400°-700° C., then drops to substantially zero after firing to about 1000° C. For $SiO_2:ZrO_2$ microparticles, firing should be carried out to an extent sufficient to form polycrystalline zirconia (e.g., tetragonal $ZrO_2$), while avoiding formation of zircon ($ZrSiO_4$) or cristobalite ($SiO_2$) crystalline microregions. Firing temperatures between about 1000° and 1100° C. are preferred.

The term "green state milling" will be used herein to describe milling of the microparticles before the ceramic metal oxide has been fired to its polycrystalline form. Use of green state milling has been found to be very beneficial in obtaining dental composites with good cure stability, particularly when both green state milling and optimization of firing temperatures is employed.

To predict cure stability for dental composites prepared from $SiO_2:ZrO_2$ microparticles, it has been found useful to evaluate the pH of the microparticles after firing by contacting an aqueous slurry of the microparticles with alizarin indicator. $SiO_2:ZrO_2$ microparticles which causes the indicator to turn yellow (pH<6) tend to form dental composites with better cure stability than $SiO_2:ZrO_2$ microparticles which cause the indicator to turn pink-red (pH<7). The aforementioned green state milling step has been found useful for making $SiO_2:ZrO_2$ microparticles which cause alizarin indicator to turn yellow.

In addition to the factors already noted above, higher firing temperatures tend to increase the hardness of the microparticles and decrease water absorption. Higher firing temperatures typically also lead to faster polymerization set times for dental composites prepared from the fired microparticles.

Firing can be carried out, for example, in a muffle furnace, with the dried powder contained in a shallow layer (e.g., 25 mm deep) in a vitreous silica boat. The fired product is then reground to provide microparticles having the desired average particle diameter, e.g., less than 50 micrometers. Regrinding can be carried out using conventional equipment and preferably employs grinding media having the same refractive index as the microparticles.

The relative molar ratio of oxide of silicon to ceramic metal oxide in the microparticles should be adjusted to provide the desired refractive index and degree of radiopacity. For the most preferred $SiO_2:ZrO_2$ microparticles, the molar ratio of $SiO_2$ to $ZrO_2$ desirably is about 2:1 or more, with values between about 3:1 and 9:1 being preferred, and values between about 5:1 and 7.5:1 being most preferred. For microparticles containing other silica:ceramic metal oxide mixtures, the ratio of silica to ceramic metal oxide should be adjusted to provide the desired degree of radiopacity coincident with attainment of the desired refractive index and other desired physical properties in the microparticles and attainment of the desired visual opacity, durability, cure stability, and other desired physical properties in dental composites prepared therewith.

The relative ratio of oxide of silicon to ceramic metal oxide can also influence polymerization set time rates for dental composites prepared therewith, with higher oxide of silicon content typically leading to faster set times.

It is particularly desirable to avoid formation within the microparticles of crystalline microregions or inhomogeneities (e.g., voids) having diameters greater than about 0.4 micrometers, a dimension which corresponds to the shortest wavelength of visible light. The presence in the microparticles of such crystalline microregions or inhomogeneities will undesirably increase the visual opacity of a dental composite prepared therewith. Thus, the microparticles of the present invention are formulated under conditions that substantially discourage or prevent the formation of such crystalline microregions and inhomogeneities. For brevity, such crystalline microregions and inhomogeneties will sometimes be referred to hereafter as "visually opacifying inclusions".

Prevention of visually opacifying inclusions can be achieved by filtering the silica starting material and/or ceramic metal oxide starting material through a microfine filter having a pore diameter less than 0.4 micrometers. A preferred filtration technique employs a series of progressively finer "Ballston" filters with the last filter in the series having a pore diameter less than about 0.2 to 0.25 micrometers. During subsequent processing, the gel formed by combination of the starting materials should be kept free of contaminants. During firing of the dried and ground solid obtained from the gel, care should be taken to avoid firing temperatures and times which might promote growth of crystalline microregions to an extent sufficient to form visually opacifying inclusions, or promote reaction between the various inorganic species within the microparticles and formation of new crystalline microregions containing visually opacifying inclusions. In general, firing temperatures above about 1100° C. tend to promote formation of visually opacifying inclusions (usually as enlarged or new crystalline microregions, or as voids or cracks) and thus should be avoided.

When used in visible light-cured dental composites of the invention, the refractive index of the microparticles preferably should be matched to the refractive index of the composite resin, e.g., within about plus or minus 0.05, more preferably within about plus or minus 0.005. With currently used resins, the microparticles preferably have a refractive index less than 1.60. A preferred method for adjusting the refractive index of the microparticles is by altering the ratio of oxide of silicon to ceramic metal oxide. The microparticle refractive index can be approximately predicted by interpolation based on a comparison of the relative volume percent of silica to ceramic metal oxide (or equivalent of ceramic metal oxide if a calcinable precursor compound is employed) in the starting mixtures. The microparticle refractive index will vary approximately linearly, based on the above volume percent comparison, between the refractive index of pure amorphous $SiO_2$ (R.I. 1.459) and that of the ceramic metal oxide when in the polycrystalline form which it adopts within the microparticle.

It is desirable to avoid the incorporation of fluxes which may cause melting of the microparticles during firing and formation of vitreous inclusions. Also, the starting mixtures preferably are substantially free of chloride ion, as chloride ion may cause dental composites containing the fired microparticles to exhibit undesirable discoloration as well as reduced shelf life.

When viewed without magnification or under optical magnification, the microparticles of the invention are a finely divided white or off-white powder having a uniform appearance. Identification of the microstructure of such microparticles preferably is carried out using transmission electron microscopy ("TEM"). Scanning electron microscopy ("SEM") typically does not reveal the microstructure adequately, since under SEM the microparticles have a uniform greyish appearance. However, under TEM the microparticle microstructure is very distinctive and can be appreciated readily.

The drawing is a TEM image of a microparticle of Example 1, at a magnification of 300,000×. The sample was prepared by mixing the microparticles with aluminum powder, compressing the mixture at a pressure of about 0.7 to 1.4 MPa, and heating the mixture to approximately 600° C. to embed the microparticles in an aluminum matrix. Slices were cut from the matrix with a diamond saw and mechanically polished to a thickness of approximately 200 micrometers. The slices were then ion beam milled (using a "Gatan" dual ion mill apparatus) to render the slices transparent to an electron beam. The ion beam milling was carried out under an argon atmosphere and both sides of the slice were milled simultaneously. During milling, the slice was rotated constantly, the gun voltage was varied from 7 KV to 4 KV, and the gun angle was varied from 15 degrees to 8 degrees. The milled slice was photographed using a JEOL Model "100CX" transmission electron microscope operated at an accelerating voltage of 100 KV.

Boundary 11 represents the outer edge of the microparticle. Circular amorphous microregions 13 contain amorphous $SiO_2$ and are generally uniformly shaded. The very slightly mottled appearance of amorphous microregions 13 is visible under TEM in the original colloidal silica aquasol particles from which the sample was prepared and may be accentuated somewhat by transmission through crystalline $ZrO_2$ microregions (not shown) within the interior of the slice. Smaller crystalline microregions 15 are darker (greyer) in color than microregions 13, and contain tetragonal $ZrO_2$. Amorphous microregions 13 are substantially uniformly dispersed with crystalline microregions 15. The microparticle appears fully dense and shows no visually opacifying inclusions. The high compressive strength of dental composites prepared therewith is thought to be due, in part, to the many grain boundaries within the microparticle. Such grain boundaries exist between adjacent amorphous and crystalline microregions, and between adjacent crystalline microregions, and serve to blunt or discourage crack propagation through the microparticle.

Typically, the dental composites of the present invention will contain chemical polymerization initiation systems such as peroxide compounds alone or in combination with suitable amines, sulfur compounds, phosphorus compounds or other chemical compounds capable of reacting with the peroxide to generate free radical species. Alternatively, the dental composites of the present invention can contain light-induced polymerization initiation systems such as ketone or alpha diketone compounds alone or in combination with suitable amines, peroxides, sulfur compounds, phosphorous compounds, or other chemical compounds capable of reacting with or being sensitized by the ketone or alpha-diketone compounds to effect polymerization of the dental composite resin. The dental composites of the present invention can also contain suitable adjuvants such as accelerators, inhibitors, stabilizers, pigments, dyes, viscosity modifiers, extending or reinforcing fillers, surface tension depressants and wetting aids, antioxidants, and other ingredients well known to those skilled in the art.

The amounts and types of each ingredient in the dental composite should be adjusted to provide the desired physical and handling properties in the composite before and after cure. For example, the cure rate, cure stability, fluidity, compressive strength, tensile strength and durability of the composite typically are adjusted by altering the types and amounts of polymerization initiators and the loading and size distribution of the microparticles. Such adjustment typically is carried out empirically based on experience with dental composites of the prior art. For use as a casting resin, the dental composite typically will contain 45 weight percent or more of the microparticles. For other applications (e.g., anterior or posterior restoratives, cavity liners, orthodontic bracket adhesives, crown and bridge cements and artificial crowns) higher microparticle loading levels typically will be employed. For maximum compressive strength (e.g., for posterior use), it is preferred that the dental composite be a "resin bonded ceramic" or "RBC". In an RBC composite, the volume of resin should be less than the void volume that would be found in a sample of the microparticles when such microparticles are in a dry, dense state. An RBC composite inherently will contain a small volume of air or other gas. An RBC composite typically will contain at least 70 volume percent or more of the microparticles, and up to 30 volume percent of resin. An RBC composite will be stronger than a composite (referred to herein as a "resin expanded" composite) which has been filled with resin to an extent sufficient to displace all voids in the composite, since in a resin expanded composite the microparticles will tend to be spaced apart rather than touching.

In a preferred embodiment, the dental composites of the present invention contain submicron silica particles, e.g., pyrogenic silicas such as the "Aerosil" "OX 50", "130", "150" and "200" silicas sold by Degussa and "Cab-O-Sil M5" silica sold by Cabot Corp. "Aerosil OX 50" is a preferred submicron silica. The submicron silica particles preferably are silane-treated to enhance wetting thereof by the resin.

Dental composites containing specified amounts of submicron silica particles and microparticles of the present invention have especially desirable handling properties in the uncured state and exceptionally high compressive strength and diametral tensile strength in the cured state. The following amounts of submicron silica particles, microparticles, and resin are preferred:

| Type of product | submicron silica, wt. % | microparticles, wt. % |
| --- | --- | --- |
| casting resin | 8–32 | 48–72 |
| cavity base | <10 | 60–80 |
| orthodontic bracket adhesive | <10 | 70–80 |
| anterior restorative | 2–16 | 64–78 |
| posterior restorative or crown material | 10–25 | 65–80 |

Optimization of compressive strength and diametral tensile strength in such products has been found to depend upon the amounts and surface areas of fillers in the composite. The following calculation is useful. In the calculation, the surface areas of the submicron silica particles and microparticles are measured before silane treatment and the indicated weight fractions are based on weights measured after silane treatment. The term "total filler" refers to the combined weight of the silane-treated submicron silica particles and silane-treated microparticles in the composite. In a first step, the surface area of the submicron silica particles is multiplied by the weight fraction of submicron silica particles in the total filler. In a second step, the surface area of the microparticles is multiplied by the weight fraction of microparticles in the total filler. The multiplication products from the first and second steps are then added together and multiplied by the weight fraction of total filler in the composite. The result, referred to herein as the "net surface area" of the composite, can be used to optimize compressive strength and diametral tensile strength independently of total filler loading. For example, for composites containing "Aerosil OX 50" submicron silica particles and $SiO_2:ZrO_2$ microparticles, compressive strength increases from a value of about 390 MPa at a net surface area of about 5 $m^2/g$, to a peak value of about 440–480 MPa at net surface areas of about 7 or more $m^2/g$; diametral tensile strength first increases and then decreases as net surface area is increased, exhibiting a value above about 75 MPa at net surface areas of about 5–22 $m^2/g$, and a value above about 90 MPa at net surface areas of about 7–15 $m^2/g$.

The dental composites of the present invention can be packaged and dispensed using means well known to those skilled in the art, e.g., multiple-part or one-part packages contained in jars, tubes, amalgamator capsules, syringes, and the like.

In addition to their use in dental composites, the microparticles of the present invention can be used in plastic composites intended for non-dental uses. Suitable resins for use in such composites include the resins already mentioned above, as well as thermosetting or thermoplastic resins such as polyester resins, acetyl resins, amino resins (e.g., urea-formaldehyde and melamine formaldehyde resins), alkyd resins, cellulosic resins (e.g., ethyl cellulose, cellulose acetate, and cellulose propionate resins), fluorocarbon resins, furane resins, polyurethane resins, phenolic resins, polyamide resins, polycarbamate resins, vinyl aromatic resins (e.g., styrene), polyolefin resins (e.g., polyethylene), and the like.

Plastic composites of the present invention can contain other adjuvants such as polymerization initiators, accelerators, inhibitors, stabilizers, pigments, dyes, viscosity modifiers, extending or reinforcing fillers, surface tension depressants and wetting aids, antioxidants, and other ingredients well known to those skilled in the art.

The microparticles of the present invention can also be used as a reinforcement agent in metal matrix composites or ceramic composites, or as abrasion resistant and/or reinforcing agents for elastomeric materials of the types described in said U.S. Pat. Nos. 3,709,706 and 3,793,041.

The following examples are offered to aid understanding of the present invention and are not to be construed as limiting the scope thereof.

EXAMPLE 1

1,065.6 grams of a 31 weight percent colloidal silica aquasol (37 Ludox LS", commercially available from E. I. du Pont De Nemours & Co.) was acidified by the addition of 11 grams of concentrated nitric acid, diluted 1:1 with dionized water, and filtered through 2 microfine filters placed in series. The first microfine filter was a "Ballston grade B" filter having a pore diameter of 2 micrometers, and the second microfine filter was a "Ballston grade AA" filter having a pore diameter of 0.25 micrometers. 492.8 Grams of aqueous zirconyl acetate (containing 25 weight percent equivalent $ZrO_2$) was similarly diluted and filtered. The aqueous zirconyl acetate was placed in a glass beaker and stirred with a nylon blade mounted on a glass rod and rotated by an air stirrer motor. The colloidal silica aquasol was poured slowly into the vortex formed in the stirred aqueous zirconyl acetate, to provide a mixture containing an equivalent $SiO_2:ZrO_2$ molar ratio of 5.5:1. The resulting mixture was stirred for 15 minutes, then poured into "Pyrex" glass rectangular cake pans to a depth of about 25 millimeters. The pans were placed in a 75° C. forced air oven for 24 hours, then removed for inspection. A loose granular powder, bluish-white in appearance, had formed in the bottom of the pans. The pans were placed in a 280° C. forced air oven for 24 hours, then removed and allowed to cool to room temperature. A weakly agglomerated powder, white in appearance, was removed from the pans and ball milled for a total milling time of 60 minutes in a ceramic mill jar containing 12 millimeter diameter by 12 millimeter long ceramic rod media. Subsequent measurements indicated that the grinding distribution obtained after 60 minutes could have been achieved with only 45 minutes of milling time. The milled powder was placed in rectangular vitreous silica saggers at a depth of about 19 millimeters and heated in a muffle furnace for 16 hours at 400° C. The temperature of the muffle furnace was then raised 100° C. every half hour. Following one half hour at 900° C., the temperature of the muffle furnace was raised to 950° C. for one hour and 1000° C. for three hours. The saggers were removed from the muffle furnace and allowed to cool in air. The resulting fired powder was weakly agglomerated and white in appearance. It was milled for 15 minutes in the ceramic ball mill described above. Subsequent measurements indicated that the grinding distribution obtained after 15 minutes could have been achieved with 5 to 10 minutes of milling time. The milled microparticles had a maximum diameter of 30 micrometers and a mean diameter of 4.5 micrometers. About 16 weight percent of the microparticles had diameters less than one micrometer. Weight loss measurements indicated no attrition of the mill liner or milling media occurred, thus indicating that the microparticles could be readily fractured using low energy input.

The microparticles were silane-treated by slurrying 100 grams of the microparticles with 200 milliliters of cyclohexane for 30 minutes. A mixture of five grams of gamma-methacryloxypropyl trimethoxysilane (commercially available from Union Carbide Corp.) and two grams n-propyl amine was added to the slurry. Mixing was allowed to continue for one hour. The slurry was then dried overnight in a fume hood followed by further drying in a forced air oven at 41° C. for one hour and at 105° C. for two hours.

A visible-light cure dental composite having especially useful performance as a posterior restorative was prepared from the silane-treated microparticles by thoroughly mixing the following ingredients:

| Ingredient | Amount, weight percent |
|---|---|
| BIS-GMA | 9.5 |
| Triethyleneglycol dimethacrylate | 9.5 |
| Silane-treated microparticles | 80.0 |
| Camphoroquinone | 0.5 |
| Dimethylaminophenethanol | 0.5 |
| | 100.0 |

A sample of the resulting composite was placed in a 4.06 mm I.D. glass tube capped with silicone plugs in each end of the tube. The tube was placed in a test rig pressurized with air at 0.28 MPa. The test rig contained two Espe "Elipar" dental curing lights aimed at opposing sides of the tube and mounted on a turntable which enabled the lights to be rotated around the tube in a 180° arc. The light guide of each curing light was spaced 3 mm from the tube wall. While operating both curing lights simultaneously and oscillating them continuously around the tube, the tube was exposed to four 20 second curing cycles from the curing lights. The tube was removed from the test rig, placed on a pair of spaced rollers, and rotated under a 110 watt "Ritter" dental operatory light at a distance of 0.6 meters for one hour. The cured sample was removed from the tube and sliced into cylinders with a diamond saw. For compressive strength testing, an 8.23 mm long cylinder was employed, and for diametral tensile strength testing a 2.21 mm long cylinder was employed. The cylinders were stored in 37° C. distilled water for 24 hours, then tested according to ADA Specification Nos. 8 and 27. The compressive strength of cured samples of the composite was 394 MPa (4,016 kilograms/cm$^2$) and the diametral tensile strength was 80 MPa (816 kilograms/cm$^2$).

Disc-shaped one millimeter thick by 20 millimeter diameter samples of the composite were cured by exposing them to illumination from an Espe "Elipar" dental curing light for 60 seconds on each side of the disk at a distance of 6 millimeters. The cured composite samples were then evaluated for visual opacity and radiopacity as follows.

Cured composite samples were measured for direct light transmission by measuring transmission of light through the thickness of the disk using a MacBeth transmission densitometer Model TD-504 equipped with a visible light filter. The densitometer value of 0.30 thereby obtained was assigned to the composite sample as its visual opacity value. Under visual examination, the cured composite samples had a greater translucency than tooth structure of comparable thickness, and readily could be pigmented to match natural dentition.

Cured composite samples were exposed to X-radiation using a Siemens "Heliodent" dental X-ray unit for 0.25 seconds at 7 milliamps and 50 kV peak voltage at a distance of about 250 millimeters. The X-ray negative was developed using a Litton "Profexray" automatic film processor. Using the Macbeth Transmission densitometer, a film density value of 1.25 to 1.30 was obtained and was assigned to the composite sample as its radiopacity value. When emplaced in a tooth and examined by X-ray, the composite readily could be distinguished from adjacent tooth structure.

Additional samples of the composite were cured in a 6 millimeter diameter by 2.5 millimeter deep cylindrical mold by exposing the samples to illumination from an Espe "Elipar" dental curing light for 20 seconds at a distance of zero millimeters. Barcol hardness testing of the top and bottom surfaces of the thus-cured samples using indenter number 934-1 (commercially available from the Barber Colman Co.) yielded average top and bottom hardness values of 81 and 80 respectively.

Repetition of the above example using starting materials that were unfiltered or filtered through filters with a pore diameter greater than 0.4 micrometers (e.g., a filter with a pore diameter of two micrometers) provided dental composites with a visual opacity of about 0.40 to 0.41. The cured composite samples had a more opaque appearance than tooth structure of comparable thickness. Addition of pigments to match tooth coloration typically would raise the visual opacity further, by about 0.01 to 0.02 visual opacity units, and would make the resulting composites noticeably more opaque than tooth structure of comparable thickness. Barcol top and bottom hardness values averaged 80 and 75, respectively, indicating that the degree of cure for such composites was less than that obtained using the filtered sol dental composite described above.

EXAMPLES 2-14

Using the method of Example 1, a variety of microparticles were prepared from unfiltered sols, formulated into two-paste chemical cure dental composites, and evaluated for visual opacity and radiopacity. The dental composites contained 70-76 weight percent microparticles, so the observed visual opacity values were in many cases lower than the value of 0.30 obtained in Example 1, and the observed radiopacity values numerically higher (i.e., less radiopaque) than the value of 1.25 to 1.30 obtained in Example 1. Set out below in Table I are the Example No., ceramic metal oxide exmployed, silica:ceramic metal oxide mole ratio, microparticle refractive index, microparticle-resin refractive index difference, visual opacity and set time for composites prepared from microparticles fired at 900° C., 950° C. or 1000° C., and radiopacity for dental composites prepared from microparticles fired at 1000° C.

Repetition of these examples using filtered sols would provide comparable or identical microparticle refractive index values, microparticle-resin refractive index difference values, and set time and radiopacity values. Visual opacity values would be lower.

TABLE I

| Ex. No. | Ceramic metal oxide | SiO$_2$:ceramic metal oxide mole ratio | Microparticle refractive index | Microparticle-resin refractive index difference | Visual opacity[1] | | | Two paste chemical cure set time, min/sec | | | Radio-pacity[1] |
|---|---|---|---|---|---|---|---|---|---|---|---|
| | | | | | 900° C. | 950° C. | 1000° C. | 900° C. | 950° C. | 1000° C. | 1000° C. |
| 2 | ZrO$_2$ | 2:1 | 1.564 | 0.024 | 0.49 | 0.50 | 0.56 | 8' | 6' | 2'45" | 0.71 |
| 3 | ZrO$_2$ | 3:1 | 1.560 | 0.020 | 0.44 | 0.44 | 0.44 | 8' | 6' | 2'30" | 0.84 |
| 4 | ZrO$_2$ | 4:1 | 1.556 | 0.016 | 0.31 | 0.32 | 0.33 | 8' | 6' | 2'30" | 0.96 |
| 5 | ZrO$_2$ | 5:1 | 1.546 | 0.006 | 0.13 | 0.22 | 0.23 | 6' | 5'30" | 2'30" | 1.11 |
| 6 | ZrO$_2$ | 5.5:1 | 1.544 | 0.004 | 0.13 | 0.13 | 0.19 | 5' | 3'30" | 2'20" | 1.21 |
| 7 | ZrO$_2$ | 6:1 | 1.542 | 0.002 | 0.14 | 0.15 | 0.18 | 4'45" | 3'15" | 2'10" | 1.29 |
| 8 | ZrO$_2$ | 6.5:1 | 1.537 | 0.003 | 0.14 | 0.16 | 0.19 | 4'30" | 3'15" | 2'00" | 1.34 |
| 9 | ZrO$_2$ | 7:1 | 1.531 | 0.009 | 0.17 | 0.20 | 0.26 | 4'15" | 3'10" | 2'00" | 1.35 |
| 10 | ZrO$_2$ | 7.5:1 | 1.531 | 0.009 | 0.18 | 0.20 | 0.28 | 3'40" | 3'10" | 1'50" | 1.40 |
| 11 | ZrO$_2$ | 8:1 | 1.529 | 0.011 | 0.21 | 0.24 | 0.28 | 3'35" | 3'05" | 1'50" | 1.40 |
| 12 | ZrO$_2$ | 9:1 | 1.525 | 0.15 | 0.23 | 0.30 | 0.34 | 3'30" | 3'00" | 1'50" | 1.41 |
| 13 | ZrO$_2$ + SrO | 7.2:1[2] | 1.524-28 | 0.016-12 | 0.26[4] | 0.33 | >0.50 | — | 1'45" | — | — |

TABLE I-continued

| Ex. No. | Ceramic metal oxide | SiO2:ceramic metal oxide mole ratio | Microparticle refractive index | Microparticle-resin refractive index difference | Visual opacity[1] | | | Two paste chemical cure set time, min/sec | | | Radio-pacity[1] |
|---|---|---|---|---|---|---|---|---|---|---|---|
| | | | | | 900° C. | 950° C. | 1000° C. | 900° C. | 950° C. | 1000° C. | 1000° C. |
| 14 | ZrO2 + BaO | 8.5:1[3] | 1.530 | 0.010 | 0.26[4] | 0.36 | 0.36 | — | 1'50" | — | — |

[1]Examples 13 and 14 had 76.6 and 76 weight percent microparticle loadings, respectively. All other Examples had 70 weight percent microparticle loadings.
[2]Based on total ceramic metal oxide. Microparticles contained SiO2:ZrO2:SrO in a 21.8:2:1 ratio. A strontium acetate solution containing 25 wt % equivalent SrO was employed as the source of SrO.
[3]Based on total ceramic metal oxide. Microparticles contained SiO2:ZrO2:BaO in a 25.8:2:1 ratio. A 25 wt % barium acetate solution was employed as the source of BaO.
[4]Greenish coloration.

EXAMPLE 15

Casting Resins

Varying amounts of the microparticles of Example 1 were combined with varying amounts of silane-treated "Aerosil OX 50" pyrogenic silica particles and a sufficient quantity of the resin of Example 1 to form composites containing 80 weight percent total filler (based on the combined weight of fillers after silane treatment) and 20 weight percent resin. The microparticles had a surface area (before silane treatment) of 5 m²/g, and the pyrogenic silica particles had a surface area (before silane treatment) of 41 m²/g. Set out below in Table II are the volume percent and weight percent of submicron silica particles, microparticles, and resin for the resulting composites, together with their compressive strength, diametral tensile strength, and visual opacity.

TABLE II

| Submicron silica | | Microparticles | | Resin | | Compressive strength, MPa | Diametral tensile strength, MPa | Visual opacity |
|---|---|---|---|---|---|---|---|---|
| Vol. % | Wt. % | Vol. % | Wt. % | Vol. % | Wt. % | | | |
| 1.81 | 2 | 62.04 | 78 | 36.15 | 20 | 396 | 78 | 0.34 |
| 2.52 | 2.8 | 61.36 | 77.2 | 36.12 | 20 | 402 | 79 | 0.36 |
| 3.61 | 4 | 60.32 | 76 | 36.07 | 20 | 400 | 84 | 0.37 |
| 7.19 | 8 | 56.89 | 72 | 35.91 | 20 | 428 | 86 | 0.38 |
| 10.72 | 12 | 53.5 | 68 | 35.77 | 20 | 446 | 91 | 0.39 |
| 14.24 | 16 | 50.15 | 64 | 35.61 | 20 | 445 | 93 | 0.39 |
| 17.73 | 20 | 46.81 | 60 | 35.46 | 20 | 445 | 91 | 0.40 |
| 21.19 | 24 | 43.5 | 56 | 35.31 | 20 | 451 | 95 | 0.39 |
| 28.02 | 32 | 36.97 | 48 | 35.01 | 20 | 456 | 92 | 0.41 |
| 34.72 | 20 | 30.56 | 40 | 34.72 | 20 | 463 | 87 | 0.41 |
| 41.33 | 48 | 24.24 | 32 | 34.43 | 20 | 477 | 88 | 0.41 |

Composites containing 4–40 weight percent submicron silica were pourable syrups in which bubbles rose to the surface, indicative of unusually low viscosity. Only a few commercially available dental composites contain 80 or more weight percent filler, and those that do are stiff, barely stirable pastes.

EXAMPLE 16

High Strength Posterior Composites

Varying amounts of the microparticles, submicron silica particles, and resin of Example 15 were combined to form RBC composites containing up to 90 weight percent total filler (based on the combined weight of fillers after silane treatment). Set out below in Table III are the volume percent and weight percent of submicron silica particles, microparticles, total filler, and resin for the resulting composites, together with their compressive strength, diametral tensile strength, and visual opacity. The composite containing 90 weight percent filler had a net surface area of:

$$[41 \text{ m}^2/\text{g}) (0.18/0.9) + (5 \text{ m}^2/\text{g}) (0.72/0.9)](0.9) = 11.2 \text{ m}^2/\text{g}.$$

TABLE III

| Submicron silica | | Microparticles | | Total filler | | Resin | | Compressive strength, MPa | Diametral tensile strength, MPa | Visual opacity |
|---|---|---|---|---|---|---|---|---|---|---|
| Vol. % | Wt. % | Vol. % | Wt. % | Vol. % | Wt. % | Vol. % | Wt. % | | | |
| 8.34 | 8.67 | 66.07 | 78.03 | 74.4 | 86.7 | 25.59 | 13.3 | 446 | 93 | 0.39 |
| 12.82 | 13.2 | 63.9 | 74.8 | 76.7 | 88 | 23.28 | 12 | 444 | 94 | 0.42 |
| 19.73 | 18.0 | 62.5 | 72.0 | 80.3 | 90 | 19.73 | 10 | 483 | 87 | 0.44 |
| 21.09 | 21.97 | 55.68 | 65.93 | 76.8 | 87.9 | 23.23 | 12.1 | 473 | 97 | 0.42 |

These composites exhibited outstanding strength values and excellent handling properties. The composite containing 90 weight percent total filler was sent to the Forsyth Dental Center in Boston, Mass. and placed in molars of *Mucacca Fasicularis* monkeys for an extended clinical study. After six months, the composite exhibited no visually detectable wear. The composite had a very desirable consistency in its uncured state. It could be tamped into a prepared tooth without excessive sticking or rebounding, and in the view of the consultant supervising the clinical study, it handled "more like amalgam" than any plastic composite he had ever encountered. An amalgam-like consistency is especially desirable since dentists have had extensive training and experience placing amalgam restorations in posterior teeth.

Various modifications and alterations will be apparent to those skilled in the art without departing from the scope and spirit of this invention, and it should be understood that this invention is not to be unduly limited to the illustrative embodiments set forth herein.

What is claimed is:
1. Radiopaque dental composite, comprising a mixture of:

(a) polymerizable resin suitable for use in the oral environment, and
(b) non-vitreous microparticles, said microparticles individually comprising:
   (i) a plurality of amorphous microregions comprising oxide of silicon, substantially uniformly interspersed with
   (ii) a plurality of crystalline microregions comprising radiopacifying polycrystalline ceramic metal oxide,
said microparticles being substantially free of visually opacifying inclusions.

2. Composite according to claim 1, wherein said resin comprises a polymerizable acrylate and said microparticles have a refractive index less than 1.60.

3. Composite according to claim 1, wherein said composite, if prepared with an 80 weight percent loading of said microparticles, exhibits a radiopacity less than or equal to 1.4 and a visual opacity less than 0.40.

4. Composite according to claim 1, wherein said amorphous microregions have diameters of about 0.002 to 0.05 micrometers, said crystalline microregions have diameters of about 0.001 to 0.01 micrometers, and 90 weight percent or more of said radiopacifying ceramic metal oxide in said microparticle is present in its polycrystalline form, and wherein said microparticles are substantially free of crystalline microregions having diameters greater than about 0.4 micrometers.

5. Composite according to claim 1, wherein said ceramic metal oxide is selected from the group consisting of $HfO_2$, $La_2O_3$, $SrO$, $ZrO_2$, and mixtures thereof.

6. Composite according to claim 1, wherein said microparticles have been prepared from sols, dispersions or solutions which have been filtered through a microfine filter having a pore diameter less than 0.4 micrometers, have been subjected to green state milling, and are substantially free of crystalline microregions having diameters greater than about 0.4 micrometers.

7. Radiopaque dental composite, comprising a one-part visible light-cure resin bonded ceramic containing a mixture of:
(a) up to 30 volume percent polymerizable resin suitable for use in the oral environment, and
(b) at least 70 volume percent non-vitreous microparticles having diameters less than about 50 micrometers and an index of refraction less than 1.60, said microparticles individually comprising:
   (i) a plurality of amorphous microregions comprising silica, substantially uniformly interspersed with
   (ii) a plurality of crystalline microregions comprising tetragonal zirconia,
said microparticles being substantially free of visually opacifying inclusions.

8. Composite according to claim 7, wherein an aqueous slurry of said microparticles will turn alizarin indicator yellow.

9. Composite according to claim 7, wherein the molar ratio of said silica to said zirconia is between 2:1 and 9:1.

10. Composite according to claim 9, wherein said ratio is between 5:1 and 7.5:1.

11. Composite according to claim 7, wherein said microparticles have been prepared from sols, dispersions, or solutions which have been filtered through a microfine filter having a pore diameter less than 0.25 micrometers, subjected to green state milling, fired to 1000° C. or more, and are substantially free of crystalline microregions having diameters greater than about 0.4 micrometers.

12. Composite according to claim 7, further comprising submicron silica particles, said composite having a net surface area of about 5–22 $m^2/g$.

13. Composite according to claim 12, containing 10–25 weight percent of said submicron silica particles, 65–80 weight percent of said microparticles, and having a net surface area of about 7–15 $m^2/g$, a compressive strength of at least 440 MPa, and a diametral tensile strength of at least 90 MPa.

14. Non-vitreous microparticles having a diameter less than about 50 micrometers, said microparticles individually comprising:
(a) a plurality of amorphous microregions comprising oxide of silicon, substantially uniformly interspersed with
(b) a plurality of crystalline microregions comprising radiopacifying polycrystalline ceramic metal oxide,
said microparticles being substantially free of visually opacifying inclusions.

15. Microparticles according to claim 14, wherein said ceramic metal oxide is selected from the group consisting of $HfO_2$, $La_2O_3$, $SrO$, $ZrO_2$ and mixtures thereof.

16. Microparticles according to claim 14, wherein said oxide of silicon comprises silica, said ceramic metal oxide comprises tetragonal zirconia, and said microparticles have an index of refraction less than 1.60 and are substantially free of crystalline microregions having diameters greater than about 0.4 micrometers.

17. Microparticles according to claim 16, wherein the molar ratio of said silica to said zirconia is between 2:1 and 9:1.

18. Microparticles according to claim 17, wherein said ratio is between 5:1 and 7.5:1.

19. A process for making a radiopaque dental composite, comprising the steps of:
(a) filtering an aqueous or organic dispersion or sol of amorphous silica through a microfine filter having a pore diameter less than 0.4 micrometers;
(b) filtering an aqueous or organic dispersion, sol, or solution of radiopacifying ceramic metal oxide, or a precursor organic or inorganic compound which is calcinable thereto, through a microfine filter having a pore diameter less than 0.4 micrometers;
(c) combining and gelling the filtered products of steps (a) and (b);
(d) heating the resulting gelled product at a temperature and pressure sufficient to remove the water or solvents therefrom without causing boiling thereof, to form a green state powder;
(e) milling said green state powder to reduce the particle size thereof;
(f) firing the resulting milled powder to convert said ceramic metal oxide or precursor compound to polycrystalline ceramic metal oxide, while preventing the growth or formation of crystalline microregions having a diameters greater than about 0.4 micrometers;
(g) milling the resulting fired powder to form microparticles which individually comprise
   (i) a plurality of amorphous microregions comprising oxide of silicon, substantially uniformly interspersed with (ii) a plurality of crystalline microregions comprising radiopacifying polycrystalline ceramic metal oxide;
(h) silane treating said microparticles to facilitate wetting thereof by polymerizable resin; and
(i) mixing the resulting silane-treated microparticles with polymerizable resin suitable for use in the oral environment to form said composite.

20. A process according to claim 19, wherein said polycrystalline ceramic metal oxide is selected from the group consisting of $HfO_2$, $La_2O_3$, SrO, $ZrO_2$, and mixtures thereof, 65–80 weight percent of said silane-treated microparticles and 10–25 weight percent of pyrogenic submicron silica particles are mixed with said polymerizable resin, and said composite has a net surface area of about 7–15 $m^2/g$, a compressive strength of at least 440 MPa, and a diametral tensile strength of at least 90 MPa.

* * * * *

UNITED STATES PATENT AND TRADEMARK OFFICE
CERTIFICATE OF CORRECTION

PATENT NO. : 4,503,169
DATED : March 5, 1985
INVENTOR(S) : Ronald M. Randklev

It is certified that error appears in the above-identified patent and that said Letters Patent is hereby corrected as shown below:

Col. 5, line 22, "If described," should read --If desired,--.

Col. 5, line 29, "effect" should read --affect--.

Col. 7, line 16, "causes" should read --cause--.

Col. 7, line 19, "(pH<7)" should read --(pH>7)--.

Col. 11, line 54, "dionized" should read --deionized--.

Col. 18, line 62, "having a diameters" should read

--having diameters--.

Signed and Sealed this

Nineteenth Day of November 1985

[SEAL]

Attest:

DONALD J. QUIGG

Attesting Officer

Commissioner of Patents and Trademarks